(12) United States Patent
Jariwala et al.

(10) Patent No.: US 6,284,843 B1
(45) Date of Patent: *Sep. 4, 2001

(54) FLUOROCHEMICAL OLIGOMER AND USE THEREOF

(75) Inventors: Chetan P. Jariwala, Woodbury; Thomas P. Klun, Lakeland, both of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/677,396

(22) Filed: Sep. 29, 2000

Related U.S. Application Data

(62) Division of application No. 09/404,747, filed on Sep. 24, 1999, now Pat. No. 6,174,964.

(51) Int. Cl.$^7$ .................. C08F 259/08; C08F 214/18; B29C 47/88
(52) U.S. Cl. .................. 525/276; 525/199; 525/200; 526/255; 524/462; 524/544; 264/22; 264/211.12
(58) Field of Search .................. 525/276, 199, 525/200; 526/255; 524/462, 544; 264/22, 211.22

(56) References Cited

U.S. PATENT DOCUMENTS

| | | | |
|---|---|---|---|
| Re. 30,782 | 10/1981 | van Turnhout | 264/22 |
| Re. 31,285 | 6/1983 | van Turnhout et al. | 55/155 |
| 2,803,615 | 8/1957 | Ahlbrecht et al. | 260/29.6 |
| 2,803,656 | 8/1957 | Ahlbrecht et al. | 260/556 |
| 2,841,573 | 7/1958 | Ahlbrecht et al. | 260/79.3 |
| 3,758,447 | 9/1973 | Falk et al. | 260/78.5 |
| 3,899,563 | 8/1975 | Oxenrider et al. | 264/211 |
| 3,971,373 | 7/1976 | Braun | 128/146.2 |
| 4,100,324 | 7/1978 | Anderson et al. | 428/288 |
| 4,302,366 | 11/1981 | Perronin et al. | 252/8.57 |
| 4,375,718 | 3/1983 | Wadsworth et al. | 29/592 |
| 4,429,001 | 1/1984 | Kolpin et al. | 428/283 |
| 4,588,537 | 5/1986 | Klaase et al. | 264/22 |
| 4,592,815 | 6/1986 | Nakao | 204/165 |
| 4,619,976 | 10/1986 | Morris et al. | 525/439 |
| 4,843,134 | 6/1989 | Kotnour et al. | 526/318.4 |
| 5,025,052 | 6/1991 | Crater et al. | 524/104 |
| 5,143,963 | 9/1992 | Sterling et al. | 524/366 |
| 5,145,727 | 9/1992 | Potts et al. | 428/198 |
| 5,147,938 | 9/1992 | Kuller | 525/276 |
| 5,149,576 | 9/1992 | Potts et al. | 428/198 |
| 5,292,796 | 3/1994 | Dams et al. | 524/598 |
| 5,300,357 | 4/1994 | Gardiner | 428/224 |
| 5,300,587 | 4/1994 | Mascia et al. | 525/359.3 |
| 5,314,959 | 5/1994 | Rolando et al. | 525/276 |
| 5,336,717 | 8/1994 | Rolando et al. | 525/64 |
| 5,380,778 | 1/1995 | Buckanin | 524/247 |
| 5,411,576 | 5/1995 | Jones et al. | 95/57 |
| 5,451,622 | 9/1995 | Boardman et al. | 524/100 |
| 5,453,540 | 9/1995 | Dams et al. | 564/96 |
| 5,459,188 | 10/1995 | Sargent et al. | 524/319 |
| 5,496,507 | 3/1996 | Angadjivand et al. | 264/423 |
| 5,508,330 | 4/1996 | Coughlin et al. | 524/251 |
| 5,536,157 | 7/1996 | Linz | 425/72.2 |
| 5,681,963 | 10/1997 | Liss | 548/455 |
| 5,705,592 | 1/1998 | Sejpka et al. | 528/42 |
| 5,898,046 | 4/1999 | Raiford et al. | 524/316 |
| 5,908,598 | 6/1999 | Rousseau et al. | 264/344 |
| 5,998,549 | 12/1999 | Milbourn et al. | 525/396 |
| 6,193,791 | * 2/2001 | Vander Louw et al. | 524/462 |

FOREIGN PATENT DOCUMENTS

| | | |
|---|---|---|
| 0670358 | 8/1998 | (EP) . |
| 3041160 | 2/1991 | (JP) . |
| 9323956 | 12/1997 | (JP) . |
| WO 97/22576 | 6/1997 | (WO) . |
| WO 97/22659 | 6/1997 | (WO) . |
| WO 97/22660 | 6/1997 | (WO) . |
| WO 98/15598 | 4/1998 | (WO) . |
| WO 98/51723 | 11/1998 | (WO) . |
| WO 98/51724 | 11/1998 | (WO) . |
| WO 98/51725 | 11/1998 | (WO) . |
| WO 98/51726 | 11/1998 | (WO) . |
| WO 98/51727 | 11/1998 | (WO) . |
| WO 99/05345 | 2/1999 | (WO) . |
| WO 00/68189 | 11/2000 | (WO) . |
| WO 00/68333 | 11/2000 | (WO) . |

OTHER PUBLICATIONS

H.C. Fielding, Organofluorine Compounds and Their Applications, R.E. Banks, Ed., *Society of Chemical Industry*, p. 214 (1979).

Chujo et al., *J. Polymer Science*, Part A, pp. 26, 2991 (1988).

Van Wente et al., "Manufacture of Super Fine Organic Fibers", *Report No. 4364 of the Naval Research Laboratories*, (May 25, 1954).

Van Wente, "Superfine Thermoplastic Fibers," *Industrial Engineering Chemistry*, vol. 48, pp. 1342–1346 (1956).

Davies, "The Separation of Airborne Dust and Particles", *Institution of Mechanical Engineers*, London Proceedings 1B, 1952.

Jariwala et al., USSN 09/405,629, filed Sep. 24, 1999, pp. 1–49.

* cited by examiner

Primary Examiner—James J. Seidleck
Assistant Examiner—Olga Asinovsky
(74) *Attorney, Agent, or Firm*—Kent S. Kokko

(57) ABSTRACT

The present invention provides a novel fluorochemical oligomer, and polymer composition comprising the fluorochemical oligomeric compound and a thermoplastic or thermoset polymer. The polymer composition is useful in preparing shaped articles such as fibers and films which have desirable oil- and water repellency properties.

20 Claims, No Drawings

FLUOROCHEMICAL OLIGOMER AND USE THEREOF

CROSS-REFERENCE TO RELATED APPLICATION

This is a divisional of application Ser. No. 09/404,747, filed Sep. 24, 1999, now U.S. Pat. No. 6,174,964.

This invention relates to fluorochemical compounds having oligomeric portions that contain pendent fluoroaliphatic and fluorine-free aliphatic groups. This invention also relates to polymer compositions comprising the fluorochemical composition and shaped articles made from the thermoplastic composition.

The utility of organofluorine compounds as surface-active agents (i.e., surfactants) and surface-treating agents is due in large part to the extremely low free-surface energy of a $C_6$–$C_{12}$ fluorocarbon group, according to H. C. Fielding, "Organofluorine Compounds and Their Applications," R. E. Banks, Ed., Society of Chemical Industry at p. 214 (1979). Generally, the organofluorine substances described above are those which have carbon-bonded fluorine in the form of a monovalent fluoroaliphatic radical such as a perfluoroalkyl group, typically —$C_nF_{2n+1}$, where n is at least 3, the terminal part of which group is trifluoromethyl, —$CF_3$.

International Published Application WO 98/51723 (Allewaert et al.) discloses fluorochemical oligomer having the formula $M^f_m M_n$—$Q^1$—$T^1$, wherein $M^f_m M_n$ represents fluorochemical oligomer comprising m units derived from fluorinated monomer and n units derived from fluorine-free monomer, m is from about 2 to 40, n is from 0 to 20, $T^1$ is —OH or —$NH_2$, and $Q^1$—$T^1$ together represent the organic residue obtained by removing a hydrogen atom from a chain transfer agent that is functionalized with $T^1$.

European Publication EP 0670358 describes polymeric surfactants having a fluorocarbon segment and a hydrocarbon segment in the molecule, which can be made by co-polymerizing a polyfluoroalkyl group-containing (meth) acrylate with a long chain (meth)acrylic alkyl ester having at least 8 carbon atoms. The polymeric surfactants are useful for making fluorine-containing-oil-in-hydrocarbon-oil type emulsions.

J. Polymer Science, Part A 1988, 26, 2991 (Chujo et al.) describes a di-carboxyl terminated macromonomer prepared by the free radical co-polymerization of a perfluoroalkyl-ethyl acrylate and methyl methacrylate in the presence of thiomalic acid. Also described is the reaction of such macromonomers with organic dicarboxylic acids and organic diamines in the presence of an appropriate catalyst to afford a copolymer wherein the macromonomer is grafted onto a polyamide chain.

Several patents have taught that the addition of certain fluorochemicals to thermoplastic imparts oil and stain repellency to thermoplastic articles such as fibers. For example, U.S. Pat. No. 5,025,052 (Crater et al.) describes the use of fluoroaliphatic radical-containing 2-oxazolidinone compounds having a monovalent fluoroaliphatic radical bonded to the 5-position thereof with an organic linking group. The compounds are said to be useful in the surface treatment of fibrous materials, such as textiles and are also useful in preparing fibers, films and molded articles by melt-extrusion or injection molding. U.S. Pat. No. 5,380,778 (Buckanin) describes the use of fluorochemical aminoalcohols in thermoplastic compositions which can be melted and shaped, for example by extrusion or molding, to provide fibers and films having desirable oil- and water-repellency properties. U.S. Pat. No. 5,451,622 (Boardman et al.) describes shaped articles, such as fibers and films, made by melt extruding mixtures of fluorochemical piperazine compounds and a thermoplastic polymer. U.S. Pat. No. 5,898,046 describes repellent compositions formed by the mixture of a thermoplastic polymer and a fluorocarbon/aliphatic hydrocarbon monoester, wherein the aliphatic hydrocarbon portion can have from about 12 to about 76 carbon atoms. International Published Application WO 97/22576 (Raiford et al.) describes fluorochemical diesters added to thermoplastic polymer melts which impart repellency of low surface tension fluids to the resultant fiber, fabric, nonwoven, film or molded article. International Published Application WO 99/05345 (Gasper et al.) discloses a hydrophobic and oleophobic fiber comprising synthetic organic polymer and a compound which is a fluorochemical ester or amide derived from a dimer or trimer acid. U.S. Pat. No. 5,411,576 (Jones et al.) describes an oily mist resistant electret filter media comprising melt-blown electret microfibers and a melt-processible fluorochemical having a melting point of at least about 25° C. and a molecular weight of about 500 to 2500, the fluorochemical being a fluorochemical piperazine, oxazolidinone or perfluorinated alkane having from 15 to 50 carbon atoms. U.S. Pat. No. 5,300,587 (Macia et al.) describes oil-repellent polymeric compositions made by blending a perfluoropolyether and a thermoplastic polymer. U.S. Pat. No. 5,336,717 (Rolando et al.) discloses fluorochemical graft copolymers derived from reacting monomers having terminal olefinic bonds with fluorochemical olefins having fluoroaliphatic groups and polymerizable double bonds.

International Published Application No. WO 98/15598 (Yamaguchi et al.) describes water-and oil-repellent resin compositions useful, e.g., for kitchenware and bathroom utensils, comprising thermoplastic or thermosetting resin and perfluoroalkylated polymer, such compositions exhibiting superior anti-fouling and mouldability. The perfluoroalkyl polymer can be a copolymer of a 5 to 18 carbon perfluoroalkyl group-containing (meth)acrylic ester and a hydrophilic group-bearing (meth)acrylic ester, with an optional copolymerizable comonomer which can be a $C_1$–$C_{25}$ (meth)acrylic acid alkyl ester, preferably a $C_8$–$C_{22}$ alkyl ester.

While these fluorochemical melt additives can in some circumstances impart satisfactory hydrophobicity and/or oleophobicity to thermoplastic resins they typically suffer from poor thermal stability above 300° C., a melt processing temperature often encountered in the industry, and they can also be prohibitively expensive, lending limitations to their commercial utility.

For many years nonwoven fibrous filter webs have been made from polypropylene using melt-blowing apparatus of the type described in Report No. 4364 of the Naval Research Laboratories, published May 25, 1954, entitled "Manufacture of Super Fine Organic Fibers" by Van Wente et al. Such melt-blown microfiber webs continue to be in widespread use for filtering particulate contaminants, e.g., as face masks and as water filters, and for other purposes, e.g., to remove oil from water.

Fibrous filters for removing particulate contaminants from the air are also made from fibrillated polypropylene films. Electret filtration enhancement can be provided by electrostatically charging the film before it is fibrillated. Common polymers such as polyesters, polycarbonates, etc. can be treated to produce highly charged electrets but these charges are usually short-lived especially under humid conditions. The electret structures may be films or sheets which find applications as the electrostatic element in electroacoustic devices such as microphones, headphones and speakers and in dust particle control, high voltage electrostatic generators, electrostatic recorders and other applications.

SUMMARY OF THE INVENTION

This invention provides a fluorochemical oligomer comprising:
(i) an oligomeric portion having both fluoroaliphatic and fluorine-free aliphatic pendent groups;
(ii) an aliphatic moiety; and
(iii) a linking group which links the oligomeric portion to the aliphatic moiety;
wherein at least one of said fluorine-free aliphatic groups or said aliphatic moiety has 22 or more carbon atoms.

This invention further provides a polymer composition comprising the fluorochemical oligomer and a thermoplastic or thermoset polymer. A polymer composition of this invention can be melted or shaped, for example by extrusion or molding, to produce shaped articles, such as fibers, films and molded articles whose surfaces exhibit excellent oil- and water repellency. The repellent polymer composition is especially useful in the preparation of nonwoven fabrics used in medical gowns and drapes, where repellency to bodily fluids is mandated. Films made from repellent polymer compositions of this invention are useful, for example, for moisture and/or grease-resistant packaging, release liners, and multilayer constructions.

In another aspect, the present invention provides oily mist resistant electret filter media comprising polypropylene electret fibers made from repellent polymer compositions of this invention, wherein the fluorinated compound has a melting temperature of at least 25° C. Preferably the fibers may be in the form of meltblown microfibers.

In another aspect, the present invention provides a method for filtering particulate material from air containing oily aerosol particles comprising passing said air through electret filter media made from repellent polymer compositions of this invention. The electret filter media of the present invention have improved electret filtration enhancement and sustain that enhancement upon exposure to oily aerosols. Furthermore, the electret filter media of the present invention maintain functional filtration enhancing charge levels under accelerated aging conditions.

Fibrous polypropylene electret filters that are currently available, some made from melt-blown polypropylene microfibers and others from fibrillated polypropylene film, can show thermally stable electret filtration enhancement. Unfortunately, fibrous electret filters made of polypropylene, whether melt-blown microfibers or fibrillated film, tend to lose their electret enhanced filtration efficiency faster than desired for some purposes when exposed to oily aerosols. There is a need to improve the long-term efficiency of air filters in the presence of aerosol oils, especially in respirators.

The novel fibrous electret filter media of the present invention are especially useful as an air filter element of a respirator such as a face mask or for such purposes as heating, ventilation, and air-conditioning. In respirator uses, the novel electret filter media may be in the form of molded or folded half-face masks, replaceable cartridges or canisters, or prefilters. In such uses, an air filter element of the invention is surprisingly effective for removing oily aerosols such as are present in cigarette smoke or in fumes from combustion engines. When used as an air filter media, such as in a respirator, the electret filter media has surprisingly better filtration performance than does a comparable electret filter media made of 100% polypropylene fibers.

DETAILED DESCRIPTION

This invention provides fluorochemical compositions comprising a thermoplastic or thermoset polymer and at least one fluorochemical oligomeric compound of Formulas I or II:

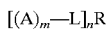  I

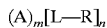  II wherein
m is 1 or 2;
n is 1 to 4 inclusive;
each L independently comprises a linking group;
each R is a saturated or unsaturated aliphatic moiety; and
each A is a fluorochemical oligomeric portion of Formula III:

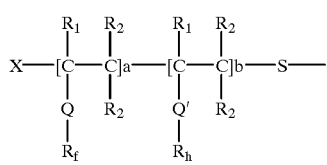

wherein the sum of a+b is a number such that A is oligomeric,
$R_1$ is hydrogen, halogen, or straight chain or branched chain alkyl containing 1 to about 4 carbon atoms;
each $R_2$ is independently hydrogen or straight chain or branched chain alkyl containing 1 to about 4 carbon atoms;
Q and Q' are each independently a covalent bond or an organic linking group,
$R_f$ is a fluoroaliphatic group, such as —$(CF_2)_7CF_3$, that comprises a fully fluorinated terminal group;
$R_h$ is a fluorine-free aliphatic group;
X is a hydrogen atom or a group derived from a free radical initiator (e.g. t-butoxy, and at least one of said R or Rh groups has 22 or more carbon atoms.

Preferably, with reference to Formulas I and II, both m and n are one to produce a fluorinated compound of Formula IV:

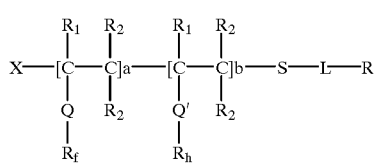

Preferably the ratio of a:b is 4:1 or more.

With reference to Formulas III and IV, it will be understood that the oligomer may have a random distribution of fluorinated and fluorine-free segments, or a sequential arrangement where the oligomer comprises "blocks" of fluorinated and fluorine-free segments. Further it will be understood that the relative position of the units derived from fluorinated monomers and fluorine-free monomers may vary with respect to the X and S moieties. In essence the following structures are both within the scope of the invention:

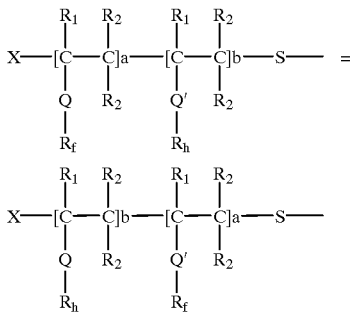

As described above and further illustrated in Formulas I–IV, a fluorochemical composition of the invention comprises a fluorinated compound that generally has three principal portions: a fluorochemical oligomeric portion "A" having pendent fluorinated and fluorine free portions, a non-polymeric linking group "L", and an aliphatic moiety "R". The oligomeric portion and the organic moiety are linked together by linking group L. The linking group may be a covalent bond, may result from a condensation reaction between a nucleophile, such as an alcohol, an amine, or a thiol, and an electrophile such as a carboxylic acid, ester, acyl halide, sulfonate ester, sulfonyl halide, cyanate, isocyanate, or may result from a nucleophilic displacement reaction between a nucleophile, such as previously described, and a moiety bearing a leaving group, such as the reaction between an alcohol (or alkoxide) and an alkyl halide (where the halogen atom of the alkyl halide serves as a leaving group).

Examples of suitable linking groups L include a covalent bond, straight chain, branched chain, or cyclic alkylene, arylene, aralkylene, oxy, oxo, hydroxy, thio, sulfonyl, sulfoxy, amino, imino, sulfonamido, carboxamido, carbonyloxy, urethanylene, urylene, and combinations thereof such as sulfonamidoalkylene.

A salient component of the oligomeric portion is the fluoroaliphatic group, designated herein as $R_f$. The fluorinated compound of the invention contains a plurality of pendent $R_f$ groups (e.g., from 4 to about 10) proximal to one another and preferably contains from about 5 percent to about 80 percent, more preferably from about 10 percent to about 65 percent, and most preferably about 12 percent to about 60 percent fluorine by weight, based on the total weight of the compound, the loci of the fluorine being essentially in the $R_f$ groups. Each $R_f$ is a stable, inert, non-polar, preferably saturated, monovalent moiety which is both oleophobic and hydrophobic. $R_f$ preferably contains at least about 3 carbon atoms, more preferably 3 to about 20 carbon atoms, and most preferably about 4 to about 14 carbon atoms. $R_f$ can contain straight chain, branched chain, or cyclic fluorinated alkylene groups or combinations thereof or combinations thereof with straight chain, branched chain, or cyclic alkylene groups. $R_f$ is preferably free of polymerizable olefinic unsaturation and can optionally contain catenary heteroatoms such as divalent oxygen, or trivalent nitrogen. It is preferred that $R_f$ contain about 40% to about 78% fluorine by weight, more preferably about 50% a to about 78% fluorine by weight. The terminal portion of the $R_f$ group contains a fully fluorinated terminal group. This terminal group preferably contains at least 7 fluorine atoms, e.g., $CF_3CF_2CF_2$—, $(CF_3)_2CF$—, or the like. Perfluorinated aliphatic groups (i.e., those of the formula $C_oF_{2o+1}$, where o is 4 to 14 are the most preferred embodiments of $R_f$).

The fluorine-free aliphatic moiety, designated $R_h$ in compounds of Formulas I–IV is a monovalent, linear or branched chain, saturated or unsaturated, cyclic or acyclic (or any combination thereof) fluorine-free aliphatic group having from 1 to 75 carbon atoms. Although not preferred, $R_h$ may contain aromatic rings. The range of structures contemplated for the organic moiety $R_h$ will be better understood with reference to the compounds suitable for use in steps of the Reaction Schemes described in detail below. Preferably $R_h$ is a linear, monovalent alkyl group of the structure —$C_nH_{2n+1}$, where n is 1 to 75, preferably 12 to 75, and most preferably 18 to 60. $R_h$ may contain catemary oxygen atoms. Where more than one $R_h$ group is present, such as in Formula II, or when n is greater than one in Formula I, the sum of the carbon atoms in the $R_h$ groups is preferably 100 carbon atoms or fewer.

The organic aliphatic moiety, designated R in compounds of Formulas I–IV is a mono-, di-, tri- or tetravalent, linear or branched chain, saturated or unsaturated, cyclic or acyclic (or any combination thereof) organic aliphatic group having from 1 to 75 carbon atoms. R may contain catemary oxygen atoms. Although not preferred, R may contain aromatic rings and may be fluorinated (i.e $R=R_f$). The valency is equivalent to the value of n in Formula I and is equal to 1 in Formula II. The range of structures contemplated for the organic moiety R will be better understood with reference to the compounds suitable for use in steps of the Reaction Schemes described in detail below. Preferably R is a linear, monovalent alkyl group of the structure —$C_nH_{2n+1}$, where n is 1 to 75, preferably 12 to 75, and most preferably 18 to 60. Where more than one R group is present, such as in Formula II, or when n is greater than one in Formula I, the sum of the carbon atoms in the R groups is preferably 100 carbon atoms or fewer.

At least one of the $R_h$ or R groups have $\geq$ 22 carbon atoms. Such compounds are novel and have enhanced oil repellency and DOP performance (when used as a melt additive in the preparation of blown microfibers for filtration).

The aliphatic backbone of the fluorochemical oligomeric portion comprises a sufficient number of polymerized units to render the portion oligomeric. The aliphatic backbone preferably comprises from 5 to about 10 polymerized units ("a" and "b" in Formula IV) derived from fluorinated and fluorine-free monomers (i.e., monomers containing a fluorinated aliphatic group $R_f$ and a fluorine-free aliphatic group $R_h$ as defined above), it is more preferred that the aliphatic backbone comprise from 5 to about 8, most preferably about 5, polymerized units.

The fluorochemical compositions of the invention generally comprise mixtures of alkylated fluorochemical oligomeric compounds. Accordingly, compounds are sometimes referred to herein as having non-integral numbers of particular substituents (e.g., "a=4.7"). In such cases the number indicates an average and is not intended to denote fractional incorporation of a substituent. The terms "oligomer" or "oligomeric" when used herein designate compounds containing a plurality of polymerized units, but fewer than that number of polymerized units present in a polymer (e.g., chains of 5 to about 20 polymerized units are to be considered "oligomeric").

The fluoroaliphatic group $R_f$ and the fluorine-free aliphatic group are each linked to the organic portion (i.e. the oligomeric backbone or the unsaturated portion of the monomer) by a linking groups designated as Q and Q' respectively in the formulas used herein. Q and Q' are independently linking groups that may be a covalent bond, divalent alkylene, or a group that can result from the condensation reaction of a nucleophile such as an alcohol, an amine, or a thiol with and electrophile, such as an ester, acid halide, isocyanate, sulfonyl halide, sulfonyl ester, or may result from a displacement reaction between a nucleophile and leaving group. Each Q and Q' is are independently chosen, preferably contains from 1 to about 20 carbon atoms and can optionally contain catenary oxygen, nitrogen, sulfur, or silicon-containing groups or a combination thereof. Q and Q' is preferably free of functional groups that substantially interfere with free-radical oligomerization (e.g., polymerizable olefinic double bonds, thiols, easily abstracted hydrogen atoms such as cumyl hydrogens, and other such functionality known to those skilled in the art). Examples of suitable linking groups Q and Q' include straight chain, branched chain, or cyclic alkylene, arylene, aralkylene; oxy, oxo, hydroxy, thio, sulfonyl, sulfoxy, amino, imino, sulfonamido, carboxamido, carbonyloxy, urethanylene, urylene, and combinations thereof such as sulfonamidoalkylene. Preferably linking group Q is a covalent bond or a sulfonamidoalkylene group. Preferably linking group Q' is a covalent bond.

Suitable linking groups Q and Q' include the following structures in addition to a covalent bond. For the purposes of this list, each k is independently an integer from 0 to about 20, $R_1'$ is hydrogen, phenyl, or alkyl of 1 to about 4 carbon atoms, and $R_2'$ is alkyl of 1 to about 20 carbon atoms. Each structure is non-directional, i.e. —$(CH_2)_kC(O)O$— is equivalent to —$O(O)C(CH_2)_k$—.

| | |
|---|---|
| —$SO_2NR_1'(CH_2)_kO(O)C$— | —$CONR_1'(CH_2)_kO(O)C$— |
| —$(CH_2)_kO(O)C$— | —$CH_2CH(OR_2')CH_2O(O)C$— |
| —$(CH_2)_kC(O)O$— | —$(CH_2)_kSC(O)$— |
| —$(CH_2)_kO(CH_2)_kO(O)C$— | —$(CH_2)_kS(CH_2)_kO(O)C$— |
| —$(CH_2)_kSO_2(CH_2)_kO(O)C$— | —$(CH_2)_kS(CH_2)_kOC(O)$— |
| —$(CH_2)_kSO_2NR_1'(CH_2)_kO(O)C$— | —$(CH_2)_kSO_2$— |
| —$SO_2NR_1'(CH_2)_kO$— | —$SO_2NR_{1'(CH_2)}k$— |
| —$(CH_2)_kO(CH_2)_k)C(O)O$— | —$(CH_2)_kSO_2NR_1'(CH_2)_kC(O)O$— |
| —$(CH_2)_kSO_2(CH_2)C(O)O$— | —$CONR_1'(CH_2)_kC(O)O$— |
| —$(CH_2)_kS(CH_2)_kC(O)O$— | —$CH_2CH(OR_2')CH_2C(O)O$— |
| —$SO_2NR'(CH_2)_kC(O)O$— | —$(CH_2)_kO$— |
| —$(CH_2)_kNR_1'C(O)O$— | —$OC(O)NR'(CH_2)_k$— |

The fluorinated compounds and fluorochemical compositions of the invention will be illustrated with reference to the embodiments shown in Formulas I–IV. In such embodiments, linking group L links the fluorochemical oligomeric portion A to the aliphatic group R. Each linking group L may be a covalent bond, a di- or polyvalent alkylene group, or a group that can result from the condensation reaction of a nucleophile such as an alcohol, an amine, or a thiol with an electrophile, such as an ester, acid halide, isocyanate, sulfonyl halide, sulfonyl ester, or may result from a displacement reaction between a nucleophile and leaving group. Each L is independently chosen, preferably contains from 1 to about 20 carbon atoms and can optionally contain catenary (i.e. in-chain) oxygen, nitrogen, sulfur, or silicon-containing groups or a combination thereof L is preferably free of functional groups that substantially interfere with free-radical oligomerization (e.g., polymerizable olefinic double bonds, thiols, easily abstracted hydrogen atoms such as cumyl hydrogens, and other such detrimental functionalities known to those skilled in the art). Examples of suitable linking groups L include straight chain, branched chain, or cyclic alkylene, arylene, aralkylene, oxy, oxo, sulfonyl, sulfoxy, amino, imino, sulfonamido, carboxamido, carbonyloxy, urethanylene, ureylene, and combinations thereof such as sulfonamidoalkylene. Preferred L groups include a covalent bond an the following structures wherein each k is independently an integer from 0 to about 20, $R_1'$ is hydrogen, phenyl, or alkyl of 1 to about 4 carbon atoms, and $R_2'$ is alkyl of 1 to about 20 carbon atoms.

| | |
|---|---|
| —$(CH_2)_kO(O)C$— | —$CH_2CH(OR_2')CH_2C(O)O$— |
| —$(CH_2)_kC(O)O$— | —$(CH_2)_kO$— |
| —$(CH_2)_kO(CH_2)_kO(O)C$— and | —$(CH_2)_kOCONH$— |

Returning now to Formulas I–IV above, $R_1$ is hydrogen, halogen (e.g., fluoro, chloro, bromo), or straight chain or branched chain alkyl of 1 to about 4 carbon atoms (e.g., methyl, ethyl, propyl, isopropyl, butyl, isobutyl, and the like). Each $R_2$ is independently hydrogen or straight chain or branched chain alkyl of 1 to about 4 carbon atoms.

X is a group derived from a free-radical initiator. As used herein, the term "free-radical initiator" designates any of the conventional compounds such as organic azo compounds, organic peroxides (e.g., diacyl peroxides, peroxyesters, dialkyl peroxides) and the like that provide initiating radicals upon homolysis. As used herein, the term "group derived from a free-radical initiator" designates an initiating radical formed upon homolytic decomposition of a free-radical initiator.

Suitable groups X include non-reactive groups such as a hydrogen atom, t-butoxy (derived from di-t-butyl peroxide), and benzoyloxy (derived from benzoyl peroxide), and reactive groups such as —$CCH_3(CN)CH_2CH_2CO_2H$ (derived from azo-4-cyanoisovaleric acid), —$C(CH_3)_2CN$ (derived from azoisobutyronitrile), and those derived from other known functional azo compounds such as 2,2'-azobis[N-(4-chlorophenyl)-2-methylpropionamidine]-dihydrochloride; 2,2'-azobis[N-(4-hydroxyphenyl)-2-methylpropionamidine] dihydrochloride; 2,2,-azobis[N-(4-aminophenyl)-2-methylpropionamidine]-tetrahydrochloride; 2,2'-azobis[2-methyl-N-2-propenylpropionamidine]dihydrochloride; 2,2'-azobis[N-(2-hydroxyethyl)-2-methylpropionamidine]-dihydrochloride; 2,2'-azobis[2-methyl-N-(2-hydroxyethyl)-propionamide]; 2,2'-azobis[2-(hydroxymethyl) propionitrile]; 2,2'-azobis[2-methyl-N-[1,1-bis (hydroxymethyl)-2-hydroxyethyl]propionamide]; and 2,2'-azobis{2-methyl-N-[1,1-bis(hydroxymethyl)ethyl]-propionamide}. Preferred groups X include those enumerated above.

The fluorochemical compounds of Formulas I, II and IV can be prepared by oligomerization of an unsaturated, fluorinated compound (V) in the presence of a free-radical initiator and chain-transfer agent of the formula $L(SH)_m$ (for m=1) according to the following Scheme:

Scheme 1

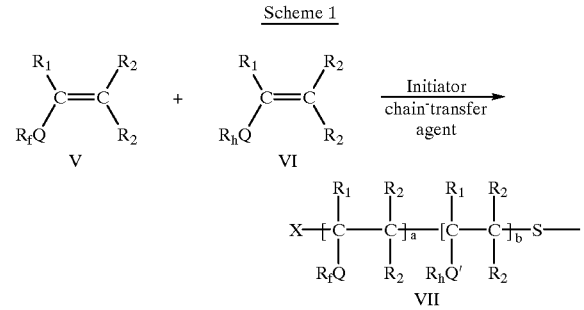

The moiety "L" corresponds to the linking group moiety L of Formula I, II and IV.

When the chain-transfer agent contains more than one sulfhydryl group, multiple oligomeric groups A may be linked through linking group L to one or more aliphatic R groups. For examples, when the chain transfer agent contains two sulfhydryl groups, two oligomeric groups A may be linked to L as follows:

Scheme 2

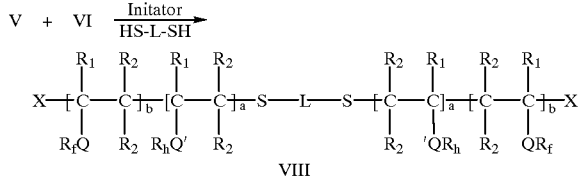

VIII

Compounds of Formula (V) and methods for the preparation thereof are known and disclosed, e.g., in U.S. Pat. No. 2,803,615 (Ahlbrecht et al.) and U.S. Pat. No. 2,841,573 (Ahlbrecht et al.) which disclosures are incorporated herein by reference. Examples of such compounds include general classes of fluorochemical monomers such as acrylates, methacrylates, vinyl ethers, and allyl compounds containing fluorinated sulfonamido groups, acrylates or ethers, and allyl compounds containing fluorinated sulfonamido groups, acrylates or methacrylates derived from fluorochemical telomer alcohols, fluorochemical thiols, and the like. Preferred compounds of Formula V includes N-methyl perfluorooctanesulfonamidoethyl acrylate, N-methyl perfluorooctanesulfonamidoethyl methacrylate, N-ethyl perfluorooctanesulfonamidoethyl acrylate, N-ethyl perfluorohexylsulfonamidoethyl methacrylate, the reaction product of isocyanatoethyl methacrylate and N-methylperfluorooctanesulfonamidoethyl alcohol, 1,1-dihydroperfluorooctyl acrylate, N-methyl perfluorooctanesulfonamidoethyl vinyl ether, $C_8F_{17}SO_2NHCH_2CH{=}CH_2$, $C_8F_{17}SO_2NCH_3CH_2CH{=}CH_2$, and others such as perfluorocyclohexyl acrylate (c-$C_6F_{11}CH_2OCOCH{=}CH_2$), and tetrameric hexafluoropropyleneoxide dihydroacrylate.

Compounds of Formula VI may be selected from alkyl acrylate esters, vinyl acetate, styrene, alkyl vinyl ethers, alkyl methacrylate esters, acrylic acid, methacrylic acid, acrylamide, methacrylamide, acrylonitrile, methacrylonitrile, and N-vinylpyrrolidone. Alkyl acrylate ester monomers useful in the invention include straight-chain, cyclic, and branched-chain isomers of alkyl esters containing $C_1$–$C_{50}$ alkyl groups. Useful specific examples of alkyl acrylate esters include: methyl acrylate, ethyl acrylate, n-propyl acrylate, 2-butyl acrylate, iso-amyl acrylate, n-hexyl acrylate, heptyl acrylate, n-octyl acrylate, iso-octyl acrylate, 2-ethylhexyl acrylate, nonyl acrylate, decyl acrylate, undecyl acrylate, dodecyl acrylate, tridecyl acrylate, and tetradecyl acrylate. Due to performance considerations, preferred alkyl acrylate esters (Rh groups) are those having from $C_{22}$–$C_{50}$ alkyl groups when the "R" groups have fewer than 22 carbon atoms. The coverse is alos true.

When the chain transfer agent $L(SH)_m$ bears a functional group, a compound of Formula VII (Scheme I) is further reacted with a functional aliphatic compound to form the linking group L and incorporate the R group into the compounds of Formulas I, II and IV. The nature of the functional groups on both the chain transfer agent and the aliphatic compounds are chosen so that they are reactive toward one another to form the L linking group. Examples of mutually reactive pairs include an acyl group (such as a carboxylic acid, acyl halide or ester) reacting with an alcohol or amine, an alcohol or an amine reacting with a "leaving group" such as a halide or tosylate, and an isocyanate reacting with an alcohol or amine.

A compound of Formulas VII or VIII can be provided with functional groups on the L linking group (in addition to the sulfhydryl group(s)) through the use of an appropriate functionalized chain-transfer agent $L(SH)_m$, wherein L contains a functional group. Suitable functional groups for inclusion in the chain-transfer agent include hydroxy, amino, halo, epoxy, haloformyl, aziridinyl, acid groups and salts thereof which react with an electrophile or nucleophile, or are capable of further transformation into such groups. The use of a functionalized chain-transfer agent allows for subsequent incorporation of the "R" group of Formulas I and II. For example, the "L" group of the chain transfer agent may be substituted with an electrophilic ester moiety. This ester moiety will allow incorporation of a long chain "R" group by further reaction with an aliphatic alcohol having a nucleophilic hydroxyl group. Reaction between the two moieties produces an ester linkage, thereby linking the fluorochemical oligomeric moiety A with the aliphatic moiety R. Alternatively, for example, the L moiety may be substituted with a hydroxyl group that may be reacted with an aliphatic ester to link the fluorochemical oligomeric moiety A with the aliphatic moiety R.

Examples of such functionalized chain transfer agents include 2-mercaptoethanol, mercaptoacetic acid, 2-mercaptobenzimidazole, 2-mercaptobenzoic acid, 2-mercaptobenzothiazole, 2-mercaptobenzoxazole, 3-mercapto-2-butanol, 2-mercaptosulfonic acid, 2-mercaptonicotinic acid, 4-hydroxythiopheno3-mercapto-1,2-propanediol, 1-mercapto-2-propanol, 2-mercaptopropionic acid, N-(2-mercaptopropionyl) glycine, 3-mercaptopropyltrimethoxysilane, 2-mercaptopyridine, 2-mercaptopyridine-N-oxide, 2-mercaptopyridinol, mercaptosuccinic acid, 2,3-mercaptopropanesulfonic acid, 2,3-dimercaptopropanol, 2,3-dimercaptosuccinic acid, cystine, cystine hydrochloride, cystine ethyl ester. Preferred functionalized chain-transfer agents include 2-mercaptoethanol, 3-mercapto-1,2-propanediol, 4-mercaptobutanol, 11-mercaptoundecanol, mercaptoacetic acid, 3-mercaptopropionic acid, 12-mercaptododecanoic acid, 2-mercaptoethylamine, 1-chloro-6-mercapto-4-oxahexan-2-ol, 2,3-dimercaptosuccinic acid, 2,3-dimercaptopropanol, 3-mercaptopropyltrimethoxysilane, 2-chloroethanethiol, 2-amino-3-mercaptopropionic acid, and compounds such as the adduct of 2-mercaptoethylamine and caprolactam.

Advantageously, the R group of Formulas I, II and IV may be incorporated by use of a non-functional chain transfer agents. Non-functionalized chain-transfer agents are those that contain a group capable of terminating a radical chain reaction (e.g., a sulfhydryl) but no further, functional groups capable of reacting with nucleophiles, electrophiles, or capable of undergoing displacement reactions. In such cases, the aliphatic portion of $L(SH)_n$ provides the aliphatic group R of Formulas I and II. Such compounds include mono, di, and polythiols such as ethanethiol, propanethiol, butanethiol, hexanethiol, n-octylthiol, t-dodecylthiol, 2-mercaptoethyl ether, 2-mercaptoimidazole, 2-mercaptoethylsulfide, 2-mercaptoimidazole, 8-mercaptomenthone, 2,5-dimercapto-1,3,4-thiadiazole, 3,4-toluenedithiol, o-, m-, and p-thiocresol, ethylcyclohexanedithiol, p-menthane-2,9-dithiol, 1,2-ethanedithiol, 2-mercaptopyrimidine, and the like. Longer chain alkyl thiols having 12 to 75 carbon atoms are preferred.

Whether functionalized or not, a chain transfer agent is present in an amount sufficient to control the number of polymerized monomer units in the oligomer. The chain transfer agent is generally used in an amount of about 0.025 to about 0.2 equivalents, per equivalent of combined olefinic monomers V and VI.

Also present in oligomerization process is a free-radical initiator as defined above in connection with X. Such compounds are known to those skilled in the art and include persulfates, azo compounds such as azoisobutyronitrile and azo-2-cyanovaleric acid and the like, hydroperoxides such as cumene, t-butyl, and t-amyl hydroperoxide, dialkyl peroxides such as di-t-butyl and dicumyl peroxide, peroxyesters such as t-butyl perbenzoate and di-t-butylperoxy phthalate, diacylperoxides such as benzoyl peroxide and lauroyl peroxide.

The initiating radical formed by an initiator can be incorporated into the fluorochemical oligomer to varying degrees depending on the type and amount of initiator used. A suitable amount of initiator depends on the particular initiator and other reactants being used. About 0.1 percent to about 5 percent, preferably about 0.1 percent, to about 0.8 percent, and most preferably about 0.2 percent to 0.5 percent by weight of an initiator can be used, based on the total weight of all other reactants in the reaction.

The oligomerization reaction of Schemes 1 and 2 can be carried out in any solvent suitable for organic free-radical reactions. The reactants can be present in the solvent at any suitable concentration, e.g., from about 5 percent to about 90 percent by weight based on the total weight of the reaction mixture. Examples of suitable solvents include aliphatic and alicyclic hydrocarbons (e.g., hexane, heptane, cyclohexane), aromatic solvents (e.g., benzene, toluene, xylene), ethers (e.g., diethylether, glyme, diglyme, diisopropyl ether), esters (e.g., ethyl acetate, butyl acetate), alcohols (e.g., ethanol, isopropyl alcohol), ketones (e.g., acetone, methyl ethyl ketone, methyl isobutyl ketone), sulfoxides (e.g., dimethyl sulfoxide), amides (e.g., N,N-dimethylformamide, N,N-dimethylacetamide), halogenated solvents such as methylchloroform, FREON™ 113, trichloroethylene, α,α,α-trifluorotoluene, fluorinated ethers such as $C_4F_9OCH_3$ and the like, and mixtures thereof The oligomerization can be carried out at any temperature suitable for conducting an organic free-radical reaction. Particular temperature and solvents for use can be easily selected by those skilled in the art based on considerations such as the solubility of reagents, the temperature required for the use of a particular initiator, and the like. While it is not practical to enumerate a particular temperature suitable for all initiators and all solvents, generally suitable temperatures are between about 30 deg. C. and about 200 deg. C.

The present invention provides a synthetic organic polymer composition comprising the one or more of the fluorinated oligomers of Formulas I and/or II and a theroplastic or thermoset organic polymer. The oligomers are useful as polymer melt additives to impart desirable low surface energy properties to the thermoplastic or thermoset polymer.

Useful polymers include both thermoplastic and thermoset polymers and include synthetic linear polyamides, e.g., nylon-6 and nylon-66, polyesters, e.g., polyethylene terephthalate, polyurethanes, epoxides, epoxy resins, acrylates, polystyrenes and polyolefins, e.g., polyethylene and polypropylene. Thermoplastic polymers such as polyolefins are preferred. The resultant articles, due to the presence of the fluorochemical oligomer, have improved oil- and water-repellency, low surface energy and a resistance to soiling.

Shaped articles (e.g., fibers, films and molded or extruded articles) of this invention can be made, e.g., by blending or otherwise uniformly mixing the alkylated fluorochemical oligomer and the polymer, for example by intimately mixing the oligomer with pelletized or powdered polymer, and melt extruding the mixture into shaped articles such as pellets, fibers, or films by known methods. The oligomer can be mixed per se with the polymer or can be mixed with the polymer in the form of a "masterbatch" (concentrate) of the oligomer in the polymer. Masterbatches typically contain from about 10% to about 25% by weight of the fluorochemical additive. Also, an organic solution of the oligomer may be mixed with the powdered or pelletized polymer, the mixture dried to remove solvent, then melted and extruded into the desired shaped article. Alternatively, molten oligomer (as a compound(s) or masterbatch) can be injected into a molten polymer stream to form a blend just prior to extrusion into the desired shaped article.

When using thermoset resins, such as epoxy resins, urethanes and acrylates, the alkylated fluorochemical oligomer may be mixed with the resin and cured by application of heat. Preferably such thermoset resins may be processed by reactive extrusion techniques such as are taught in U.S. Pat. No. 4,619,976 (Kotnour) and U.S. Pat. No. 4,843,134 (Kotnour) the disclosures of which are herein incorporated by reference.

The thermoplastic composition containing alkylated fluorochemical oligomeric compounds of the present invention may be used to provide oil and water repellency to fibers. The fluorochemical oligomers are melt processible, i.e., suffer substantially no degradation under the melt processing conditions used to form the fibers. The fluorochemical oligomers preferably have a molecular weight in the range of about 1000 to 10,000, more preferably in the range of about 1500 to 5000. The fluorochemical oligomer is preferably substantially free from mobile polar and/or ionic species, contaminants and impurities which could increase the electrical conductivity or otherwise interfere with the ability of the fibers to accept and hold electrostatic charges.

The amount of oligomer in the composition is that amount sufficient to produce a shaped article having a surface with the desired properties of oil and water repellency and/or soiling resistance. Preferably, the amount of oligomer will be that amount which provides from about 100 to 10,000 ppm fluorine, more preferably 200 to 5000 ppm, most preferably 400 to 3000 ppm fluorine, based on the weight of the shaped article.

After melt extrusion of a fiber, film or extruded article, an annealing step may be carried out to enhance oil and water repellency. Annealing apparently allows the fluorochemical oligomer to migrate to the surface of the thermoplastic polymer with a resultant increase in repellency properties, reduced surface activity, improved solvent resistance and improved release properties. The fiber or film is annealed for at a temperature and for a time sufficient to increase the amount of fluorochemical oligomer at the surface. Effective time and temperature will bear an inverse relationship to one another and a wide variety of conditions will be suitable. Using polypropylene, for example, the annealing process can be conducted below the melt temperature at about 50° to 120° C. for a period of about 30 seconds to 10 minutes. Annealing may also be effected by contact with heated rolls, such as embossing rolls, at 50° C. to 160° C. for periods of about 1 to 30 seconds. In some cases, the presence of moisture during annealing, e.g., by using an autoclave to anneal, can improve the effectiveness of the fluorochemical oligomer. The annealing method may also serve to reduce the amount of oligomer necessary by maximizing fluorine content at the surface of the polymer.

In addition to their use in modifying the properties of fibers, the polymer composition of the invention is also useful in preparing blown microfibers for non-woven fabrics having low surface energy, oil and water repellency and/or soiling resistance. The resin, such as polypropylene, used to form the melt blown microfibers should be substantially free from materials such as antistatic agents which could increase the electrical conductivity or otherwise interfere with the ability of the fibers to accept and hold electrostatic charges. When the fluorochemical compounds of the invention are used as additives to melt blown microfibers, the additive is preferably present in amounts of about 0.2 to 10 weight percent, more preferably from 0.5 to 5 weight percent and most preferably 0.5 to 2 weight percent.

As used herein, the terms "fiber" and "fibrous" refer to particulate matter, generally thermoplastic resin, wherein the length to diameter ratio of the particulate matter is greater than or equal to about 10. Fiber diameters may range from about 0.5 micron up to at least 1,000 microns. Each fiber may have a variety of cross-sectional geometries, may be solid or hollow, and may be colored by, e.g., incorporating dye or pigment into the polymer melt prior to extrusion.

The non-woven webs of fibers of thermoplastic olefinic polymer for use in this invention include non-woven webs manufactured by any of the commonly known processes for producing non-woven webs. For example, the fibrous non-woven web can be made by spunbonding techniques or melt-blowing techniques or combinations of the two. Spunbonded fibers are typically small diameter fibers which are formed by extruding molten thermoplastic polymer as filaments from a plurality of fine, usually circular capillaries of a spinneret with the diameter of the extruded fibers being rapidly reduced. Meltblown fibers are typically formed by extruding the molten thermoplastic material through a plurality of fine, usually circular, die capillaries as molten threads or filaments into a high velocity, usually heated gas (e.g air) stream which attenuates the filaments of molten thermoplastic material to reduce their diameter. Thereafter, the meltblown fibers are carried by the high velocity gas stream and are deposited on a collecting surface to form a web of randomly disbursed meltblown fibers. Any of the non-woven webs may be made from a single type of fiber or two or more fibers which differ in the type of thermoplastic olefinic polymer and/or thickness. Alternatively, sheath-core fibers can be extruded, containing different polymer compositions in each layer or containing the same polymer composition in each layer but employing the more expensive fluorochemical component in the outer sheath layer.

The melt blown polypropylene microfibers useful in the present invention can be prepared as described in Van Wente, A., "Superfine Thermoplastic Fibers," Industrial Engineering Chemistry, vol. 48, pp. 1342–1346 (1956) and in Report No. 4364 of the Naval Research Laboratories, published May 25, 1954, entitled "Manufacture of Super Fine Organic Fibers" by Van Wente et al. or from microfiber webs containing particulate matter such as those disclosed, for example, in U.S. Pat. No. 3,971,373 (Braun), U.S. Pat. No. 4,100,324 (Anderson) and U.S. Pat. No. 4,429,001 (Kolpin et al.), which patents are incorporated herein by reference. Multilayer constructions of nonwoven fabrics enjoy wide industrial and commercial utility and include uses such as fabrics for medical gowns and drapes. The nature of the constituent layers of such multilayer constructions can be varied according to the desired end use characteristics, and can comprise two of more layers of melt-blown and spun-bond webs in may useful combinations such as described in U.S. Pat. Nos. 5,145,727 and 5,149,576, both descriptions of which are incorporated herein by reference. The filtering efficiency of a melt-blown microfiber web can be improved by a factor of two or more when the melt-blown fibers are bombarded as they issue from the orifices with electrically charged particles such as electrons or ions, thus making the fibrous web an electret. Similarly, the web can be made an electret by exposure to a corona after it is collected. Melt-blown polypropylene microfibers are especially useful, while other polymers may also be used such as polycarbonates and polyhalocarbons that may be melt-blown and have appropriate volume-resistivities under expected environmental conditions.

Any of a wide variety of constructions, especially multi-layer constructions such as SMS (spunbond/meltblown/spunbond) constructions, may be made from the above-described fibers and fabrics, and such constructions will find utility in any application where some level of hydrophobicity, oleophobicity (or other fluid repellency, such as to bodily fluids) is required. The fibers prepared from the synthetic organic polymer composition of the invention may be used in woven and nonwoven medical fabrics (such as drapes, gowns and masks), industrial apparel, outdoor fabrics (such as umbrellas, awning, tents, etc), raincoats and other outdoor apparel, as well as home furnishings such as table linens and shower curtains, and in myriad other related uses.

Preferably, the filter media is annealed, i.e., heated for a sufficient time at a sufficient temperature to cause the fluorochemical additive to bloom to the surface of the fibers. Generally, about 1 to 10 minutes at about 140 deg. C. is sufficient although shorter times may be used at higher temperatures and longer times may be required at lower temperatures.

Blown microfibers for fibrous electret filters of the invention typically have an effective fiber diameter of from about 5 to 30 micrometers, preferably from about 7 to 10 micrometers, as calculated according to the method set forth in Davies, C. N., "The Separation of Airborne Dust and Particles," Institution of Mechanical Engineers, London, Proceedings 1B, 1952.

The electret filter media of the present invention preferably has a basis weight in the range of about 10 to 500 g/m$^2$, more preferably about 10 to 100 g/m$^2$. In making melt-blown microfiber webs, the basis weight can be controlled, for example, by changing either the collector speed or the die throughput. The thickness of the filter media is preferably about 0.25 to 20 mm, more preferably about 0.5 to 2 mm. The electret filter media and the polypropylene resin from which it is produced should not be subjected to any unnecessary treatment which might increase its electrical conductivity, e.g., exposure to gamma rays, ultraviolet irradiation, pyrolysis, oxidation, etc.

The melt-blown microfibers or fibrillated fibers of the electret filters of the invention can be electrostatically charged by a process described in U.S. Pat. No. Re. 30,782 (van Turnhout) or Re. 31,285 (van Turnhout) or by other conventional methods for charging or polarizing electrets, e.g., by a process of U.S. Pat. No. 4,375,718 (Wadsworth et al.); U.S. Pat. No. 4,588,537 Klasse et al.); or U.S. Pat. No. 4,592,815 (Nakao). In general, the charging process involves subjecting the material to corona discharge or pulsed high voltage.

Films prepared from the composition of this invention can be made which are useful, for example, for grease-resistant packaging, release liners and microporous film applications. These films can be used to make multi-layer constructions in which one, more than one, or all layers contain the fluorochemical oligomeric compound.

This invention is illustrated by, but is not intended to be limited to, the following examples. Unless otherwise specified, all percentages shown in the examples and test methods, which follow, are percentages by weight.

Glossary

UNILIN™ 700—polyethylene 700 alcohol (having about 50 carbon atoms), available from Baker Petrolite Corp., Tulsa, Okla.

UNILI™ 700A—To a three necked round bottom flask equipped with a mechanical stirrer and a Dean-Stark apparatus was added 200 g (0.231 mol) of UNILIN™ 700, 16.7 g (0.231 mol) of acrylic acid, 2 g of methanesulfonic acid and 400 mL of toluene. The resulting mixture was heated to reflux for approximately 15 hours, during which time water had collected in the Dean-Stark apparatus. IR of the reaction product showed no —COOH and —OH peaks, indicating that the ester formation was complete. To the hot ester solution was slowly added 10 g of $Ca(OH)_2$ while stirring. and then hot filtered. The resulting mixture was filtered hot, the toluene was removed from the filtrate by heating under reduced pressure, and the remaining wet solid was dried in a vacuum oven. Also available as X-8503™ from Baker-Petrolite, Tulsa, Okla.

UNILIN™ 425—polyethylene 460 alcohol (having about 32 carbon atoms), available from Baker Petrolite Corp.

UNILIN™ 425A—To a three necked round bottom flask equipped with a mechanical stirrer and a Dean-Stark apparatus was added 150 g (0.280 mol) of UNILIN™ 425, 20.2 g (0.280 mol) of acrylic acid, 1.5 g of methanesulfonic acid and 300 mL of toluene. The resulting mixture was heated to reflux for approximately 15 hours, during which time water had collected in the Dean-Stark apparatus. Infrared spectra (IR) of the reaction product showed no —COOH and —OH peaks, indicating that the ester formation was complete. To the hot ester solution was slowly added 10 g of $Ca(OH)_2$ while stirring. The resulting mixture was filtered hot, the toluene was removed from the filtrate by heating under reduced pressure, and the remaining wet solid was dried in a vacuum oven.

stearyl alcohol—$C_{18}H_{37}OH$, available from Aldrich Chemical Co., Milwaukee, Wis.

behenyl alcohol (Henkel 3302), Henkel Cincinnati, Ohio.

ODA—octadecyl acrylate, $C_{18}H_{37}OC(O)CH=CH_2$, available from Aldrich Chemical Co.

UNICID™ 700—polyethylene 700 acid (having around 50 carbon atoms), available from Petrolite Corp., St Louis, Mo.

EMPOL™ 1008—distilled and hydrogenated dimer acid made from oleic acid, having an acid equivalent weight of 305 as determined by titration, available from Henkel Corp./Emery Group, Cincinnati, Ohio.

dodecyl mercaptan—$C_{12}H_{25}SH$, available from Aldrich Chemical Co.

octadecyl mercaptan—$C_{18}H_{37}SH$, available from Aldrich Chemical Co.

3-mercaptopropionic acid—$HSCH_2CH_2COOH$, available from Aldrich Chemical Co.

methyl 3-mercaptopropionate—$HSCH_2CH_2COOCH_3$, available from Aldrich Chemical Co.

AIBN—2,2'-azobisisobutyronitrile, available as VAZO™ 64 initiator from E. I. duPont de Nemours & Co., Wilmington, Del.

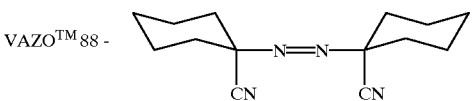

VAZO™ 88 initiator, available from E. I. duPont de Nemours & Co.

MeFOSE—$C_8F_{17}SO_2N(CH_3)CH_2CH_2OH$, can be prepared using the general procedure described in Example 3 of U.S. Pat. No. 2,803,656.

MeFOSEA—$C_8F_{17}SO_2N(CH_3)C_2H_4OC(O)CH=CH_2$, can be prepared using the general procedure described in U.S. Pat, No. 2,803,615.

MeFBSEA—$C_4F_9SO_2N(CH_3)CH_2CH_2OC(O)CH=CH_2$, can be prepared using the general procedure described in U.S. Pat. No. 2,803,615.

MeFBSEMA—$C_4F_9SO_2N(CH_3)C_2H_4OC(O)C(CH_3)=CH_2$, can be prepared using the general procedure described in U.S. Pat, No. 2,803,615.

FC Oxazolidinone A—a polymer melt additive prepared by reacting $C_8F_{17}SO_2N(CH_3)CH(OH)CH_2Cl$ with stearyl isocyanate at a 1:1 molar ratio followed by ring closure using essentially the same procedure as described in Scheme I of U.S. Pat. No. 5,025,052 (Crater et al.).

FC Oxazolidinone B—a polymer melt additive prepared by reacting $C_8F_{17}SO_2N(Me)CH(OH)CH_2Cl$ with hexamethylene diisocyanate at a 2:1 molar ratio followed by ring closure using essentially the same procedure as described in Scheme I of U.S. Pat. No. 5,025,052 (Crater et al.).

(MeFOSE)$_2$-EMPOL™ 1008—To a 500 mL 2-necked round-bottom flask equipped with overhead condenser, thermometer and Dean-Stark trap wrapped with heat tape was charged 57.8 g (0.190 eq) of Empol™ 1008 dimer acid, 100 g (0.185 eq) of MeFOSE, 1 g of p-toluenesulfonic acid and 50 g of toluene. The resulting mixture was placed in an oil bath heated to 150° C. The degree of esterification was monitored by measuring the amount of water collected in the Dean-Stark trap and also by using gas chromatography to determine the amount of unreacted fluorochemical alcohol. After 18 hours of reaction, about 2.8 mL of water was collected and a negligible amount of fluorochemical alcohol remained, indicating a complete reaction. The reaction mixture was then cooled to 100° C. and was twice washed with 120 g aliquots of deionized water to a water pH of 3. The final wash was removed from the flask by suction, and the reaction mixture was heated to 120° C. at an absolute pressure of about 90 torr to remove volatiles. The product, a brownish solid, was characterized as containing the desired product by $^1H$ and $^{13}C$ NMR spectroscopy and thermogravimetric analysis.

MeFOSE-UNICID™ 700—To a 3-necked round bottom flask equipped with a mechanical stirrer and Dear-Stark apparatus was added 135 g (0.242 mol) of MeFOSE, 215.7 g (0.242 mol) of UNICID™ 700, 3.5 g of methanesulfonic acid and 400 mL of toluene. The resulting mixture was heated to reflux for approximately 15 hours, during which time water had collected in the Dean-Stark apparatus. IR spectra of this mixture showed no —COOH or —OH peaks. To this hot mixture 10 g of $Ca(OH)_2$ was added slowly with stirring, and the hot solution was filtered. Toluene was removed from the filtrate by heating under reduced pressure, and the remaining solids were dried in a vacuum oven.

PP3505—ESCORENE™ PP3505 polypropylene, having a 400 melt index flow rate, available from Exxon Chemical Co., Baytown, Tex.

Preparation of Fluorochemical Oligomeric Compounds and Intermediates

MeFOSEA)$_4$(ODA)$_1$-SCH$_2$CH$_2$COOCH$_3$—To a round bottom flask equipped with stirrer, thermometer, reflux condenser and nitrogen bubbler was added 122.5 g (0.2 mol) of MeFOSEA monomer, 16.2 g (0.05 mol) of ODA and 150 mL of ethyl acetate. While stirring, nitrogen was bubbled through the resulting solution for 15 minutes. Then to this solution was added 6.0 g (0.05 mol) of methyl 3-mercaptopropionate, and nitrogen was bubbled into the solution for another 2 minutes. 0.5 wt % of AIBN was added and the resulting mixture was heated to 65° C. for about 15 hours under a nitrogen atmosphere. IR spectra of this material showed the absence of >C=C< peak at 1637 cm$^{-1}$, indicating no residual monomer. The reaction product was poured into a 50:50 blend of methyl alcohol and hexanes, and the white powder which precipitated was filtered and dried for about 5–6 hours at 50–60° C. under vacuum. TGA of this material showed onset of thermal degradation in air at 346° C. The calculated average number of polymerized monomer units per polymer chain is 5.

(MeFOSEA)$_4$(UNILIN™425A)$_1$-SCH$_2$CH$_2$COOCH$_3$ — To a round bottom flask equipped with stirrer, thermometer, reflux condenser and nitrogen bubbler was added 122.5 g (0.2 mol) of MeFOSEA monomer, 29.4 g (0.05 mol) of UNILIN™425A and 160 mL of methyl isobutyl ketone (MIBK). While stirring at 90° C., nitrogen was bubbled through the resulting solution for 15 minutes. Then to this solution was added 6.0 g (0.05 mol) of methyl 3-mercaptopropionate, and nitrogen was bubbled into the solution for another 2 minutes. 0.8% (wt) of VAZO™88 was added and the resulting mixture was heated to 95–100° C. for about 24 hours under a nitrogen atmosphere. IR spectra of this material showed the absence of >C=C< peak at 1637 cm$^{-1}$, indicating no residual monomer. The MIBK was evaporated under reduced pressure. The calculated average number of polymerized monomer units per polymer chain is 5.

(MeFOSEA)$_4$(UNILIN™ 700A)$_1$-SCH$_2$CH$_2$COOCH$_3$— This random copolymer was prepared using essentially the same procedure as described for preparing (MeFOSEA)$_4$(UNILIN™ 425A)$_1$-SCH$_2$CH$_2$COOCH$_3$, except that the UNILIN™ 425A was replaced with an equimolar amount of UNILIN™ 700A. The calculated average number of polymerized monomer units per polymer chain is 5.

(MeFBSEA)$_4$(UNILIN™ 700A)$_1$-S—CH$_2$CH$_2$COOCH$_3$—This random copolymer was prepared using essentially the same procedure as described for preparing (MeFOSEA)$_4$(UNILIN™ 425A)$_1$-SCH$_2$CH$_2$COOCH$_3$, except that the UNILIN™ 425A was replaced with an equimolar amount of UNILIN™ 700A and the MeFOSEA was replaced with an equimolar amount of MeFBSEA. The calculated average number of polymerized monomer units per polymer chain is 5.

(MeFBSEMA)$_4$(UNILIN™ 700A)$_1$-S—CH$_2$CH$_2$COOCH$_3$—This random copolymer was prepared using essentially the same procedure as described for preparing (MeFOSEA)$_4$(UNILIN™ 425A)$_1$-SCH$_2$CH$_2$COOCH$_3$, except that the UNILIN™ 425A was replaced with an equimolar amount of UNILIN™ 700A and the MeFOSEA was replaced with an equimolar amount of MeFBSEMA. The calculated average number of polymerized monomer units per polymer chain is 5.

(MeFBSEMA)$_4$(UNILIN™ 700A)$_1$, high molecular weight—This random copolymer was prepared using essentially the same procedure as described for preparing (MeFOSEA)$_4$(UNILIN™ 700A)$_1$-SCH$_2$CH$_2$COOCH$_3$, except that no chain transfer agent (methyl 3-mercaptopropionate) was used. The resulting molecular weight was not measured but is believed to be considerably higher than when the chain transfer agent was employed.

(MeFOSEA)$_4$(ODA)$_1$-S—CH$_2$CH$_2$COOH—To a round bottom flask equipped with stirrer, thermometer, reflux condenser and nitrogen bubbler was added 122.5 g (0.2 mol) of MeFOSEA, 16.2 g (0.05 mol) of ODA, and 150 mL of ethyl acetate. The contents of the flask were stirred to form a solution, and nitrogen was bubbled through the solution for 15 minutes. To this solution was then added 5.3 g (0.05 mol) of 3-mercaptopropionic acid (available from Aldrich Chemical Co.), and nitrogen was bubbled through the contents of the flask for an additional 2 minutes. 0.5 wt % of AIBN was added, and the resulting mixture was heated to 65° C. for approximately 15 hours under a nitrogen atmosphere. IR spectra of this material showed the absence of a >C=C< peak at 1637 cm$^{-1}$, indicating the absence of the monomers. The polymer solution was poured in hexanes, causing the polymer to precipitate as a white powder, which was removed by filtration and dried at 50–60° C. under vacuum.

(MeFOSEA)$_4$(ODA)$_1$-S—CH$_2$CH$_2$COO-UNILIN™ 700—To a 3-necked round bottom flask equipped with a mechanical stirrer and Dear-Stark apparatus was added 50 g (0.0174 mol) of (MeFOSEA)$_4$(ODA)$_1$-S—CH$_2$CH$_2$COOH, 15 g (0.0174 mol) of UNILIN™ 700 alcohol, 1 mL of methanesulfonic acid and 100 mL of toluene. The resulting mixture was heated to reflux for approximately 15 hours, during which time some water had collected in the Dean-Stark apparatus. IR spectra of this mixture showed no —COOH or —OH peaks. To this hot mixture, 5 g of Ca(OH)$_2$ was slowly added with stirring, and the resulting hot solution was filtered. Toluene was removed from the filtrate by heating under reduced pressure, and the remaining solids were dried in a vacuum oven.

(MeFOSEA)$_4$(ODA)$_1$-S—CH$_2$CH$_2$COO-UNILIN™ 425—This ester was prepared using essentially the same procedure as described for preparing (MeFOSEA)$_4$(ODA)$_1$-S—CH$_2$CH$_2$COO-UNILIN™ 700, except that the UNILIN™ 700 Alcohol was replaced with an equimolar amount of UNILIN™ 425 Alcohol.

(MeFOSEA)$_4$(ODA)$_1$-S—CH$_2$CH$_2$COO—C$_{18}$H$_{37}$— This ester was prepared using essentially the same procedure as described for preparing (MeFOSEA)$_4$(ODA)$_1$-S—CH$_2$CH$_2$COO-UNILIN™ 700, except that the UNLIN™ 700 Alcohol was replaced with an equimolar amount of stearyl alcohol.

(MeFOSEA)$_4$(ODA)$_1$-S—CH$_2$CH$_2$COO—C$_{22}$H$_{45}$— This ester was prepared using essentially the same procedure as described for preparing (MeFOSEA)$_4$(ODA)$_1$-S—CH$_2$CH$_2$COO-UNILIN™ 700, except that the UNILIN™ 700 Alcohol was replaced with an equimolar amount of behenyl alcohol.

(MeFOSEA)$_4$(ODA)$_1$-S—CH$_2$CH$_2$COO-MeFOSE—To a 3-necked round bottom flask equipped with a mechanical stirrer and Dear-Stark apparatus was added 60 g (0.0208 mol) of (MeFOSEA)$_4$(ODA)$_1$-S—CH$_2$CH$_2$COOH, 11.6 g (0.0208 mol) of MeFOSE, 1 mL of methanesulfonic acid and 100 mL of toluene. The resulting mixture was heated to reflux for approximately 15 hours, during which time some water had collected in the Dean-Stark apparatus. IR spectra of this mixture showed no —COOH or —OH peaks. To this hot mixture 5 g of Ca(OH)$_2$ was slowly added with stirring, and the hot solution was filtered. Toluene was removed from the filtrate by heating under reduced pressure, and the remaining solids were dried in a vacuum oven.

(MeFOSEA)$_4$(ODA)$_1$-SC$_{12}$H$_{25}$—To a round bottom flask equipped with stirrer, thermometer, reflux condenser and nitrogen bubbler was added 122.5 g (0.2 mol) of MeFOSEA, 16.2 g (0.05 mol) of ODA and 150 mL of ethyl acetate. While stirring, nitrogen was bubbled through the resulting solution for 15 minutes. Then to this solution was added 10.1 g (0.05 mol) of dodecyl mercaptan, and nitrogen was bubbled into the solution for an additional 2 minutes. 0.5% (wt) of AIBN was added and the resulting mixture was heated to 65° C. for about 15 hours under a nitrogen atmosphere. IR spectra of this material showed the absence of >C=C< peak at 1637 cm$^{-1}$, indicating no residual monomer. The reaction product was poured into a 50:50 blend of methyl alcohol and hexanes, and the white powder which precipitated was filtered and dried for about 5–6 hours at 50–60° C. under vacuum. The calculated average number of polymerized monomer units per polymer chain is 5.

(MeFOSEA)$_4$(ODA)$_1$-SC$_{18}$H$_{37}$—To a round bottom flask equipped with stirrer, thermometer, reflux condenser and nitrogen bubbler was added 122.5 g (0.2 mol) of MeFOSEA, 16.2 g (0.05 mol) of ODA and 150 mL of ethyl acetate. While stirring, nitrogen was bubbled through the resulting solution for 15 minutes. Then to this solution was added 14.3 g (0.05 mol) of octadecyl mercaptan, and nitrogen was bubbled into the solution for an additional 2 minutes. 0.5% (wt) of AIBN was added and the resulting mixture was heated to 65° C. for about 15 hours under a nitrogen atmosphere. IR spectra of this material showed the absence of >C=C< peak at 1637 cm$^{-1}$, indicating no residual monomer. The reaction product was poured into a 50:50 blend of methyl alcohol and hexanes, and the white powder which precipitated was filtered and dried for about 5–6 hours at 50–60° C. under vacuum. The calculated average number of polymerized monomer units per polymer chain is 5.

(MeFOSEA)$_4$(UNILIN™ 700A)$_1$-SC$_{18}$H$_{37}$—This random copolymer was prepared using essentially the same procedure as described for preparing (MeFOSEA)$_4$(UNILIN 425A)$_1$-SCH$_2$CH$_2$COOCH$_3$, except that the UNILIN 425A was replaced with an equimolar amount of UNILIN™ 700A and the HSCH$_2$CH$_2$CO$_2$CH$_3$ was replaced by an equimolar amount of HSC$_{18}$H$_{37}$. The calculated average number of polymerized monomer units per polymer chain is 5.

Test Methods

Melt-Blown Extrusion Procedure—The melt-blown extrusion procedure used is the same as described in U.S. Pat. No. 5,300,357, column 10, which is herein incorporated by reference. The extruder used is a Brabender 42 mm conical twin screw extruder, with maximum extrusion temperature of 270–280° C. and distance to the collector of 12 inches (30 cm).

Fluorochemical and thermoplastic polymer mixtures are mixed by blending the thermoplastic polymer and fluorochemical polymer melt additive (if used) in a paperboard container using a mixer head affixed to a hand drill for about one minute until a visually homogeneous mixture is obtained.

The process condition for each mixture is the same, including the melt blowing die construction used to blow the microfiber web, the basis weight of the web (55±5 g/m$^2$) and the diameter of the microfibers (5–18 micrometers). Unless otherwise stated, the extrusion temperature (i.e. die temperature) is 270–280° C., the primary air temperature is 270° C., the pressure is 124 kPa (18 psi), with a 0.076 cm air gap width, and the polymer throughput rate is about 180 g/hr/cm.

Water Repellency Test—Nonwoven web samples were evaluated for water repellency using 3M Water Repellency Test V for Floorcoverings February 1994), available from 3M Company. In this test, samples are challenged to penetrations by blends of deionized water and isopropyl alcohol (IPA). Each blend is assigned a rating number as shown below:

| Water Repellency Rating Number | Water/IPA Blend (% by volume) |
|---|---|
| 0 | 100% water |
| 1 | 90/10 water/IPA |
| 2 | 80/20 water/IPA |
| 3 | 70/30 water/IPA |
| 4 | 60/40 water/IPA |
| 5 | 50/50 water/IPA |
| 6 | 40/60 water/IPA |
| 7 | 30/70 water/IPA |
| 8 | 20/80 water/IPA |
| 9 | 10/90 water/IPA |
| 10 | 100% IPA |

In running the Water Repellency Test, a nonwoven web sample is placed on a flat, horizontal surface. Five small drops of water or a water/IPA mixture are gently placed at points at least two inches apart on the sample. If, after observing for ten seconds at a 45° angle, four of the five drops are visible as a sphere or a hemisphere, the nonwoven web sampled to pass the test. The reported water repellency rating corresponds to the highest water or water/IPA mixture for which the nonwoven sample passes the described test.

It is desirable to have a water repellency rating of at least 4, preferably a rating at least 6.

Oil Repellency Test—Nonwoven web samples were evaluated for oil repellency using 3M Oil Repellency Test III (February 1994), available from 3M Company, St. Paul, Minn. In this test, samples are challenged to penetration by oil or oil mixtures of varying surface tensions. Oils and oil mixtures are given a rating corresponding to the following.

| Oil Repellency Rating Number | Oil Composition |
|---|---|
| 0 | (fails Kaydol ™ mineral oil) |
| 1 | Kaydol ™ mineral oil |
| 2 | 65/35 (vol) mineral oil/n-hexadecane |
| 3 | n-hexadecane |
| 4 | n-tetradecane |
| 5 | n-dodecane |
| 6 | n-decane |
| 7 | n-octane |
| 8 | n-heptane |

The Oil Repellency Test is run in the same manner as is the Water Repellency Test, with the repellency rating corresponding to the highest oil or oil mixture for which the nonwoven web sample passes the test.

It is desirable to have an oil repellency rating of at least 1, preferably a rating of at least 3.

DOP Wetting Time Test—Nonwoven webs were challenged to resistance to Dioctyl phthalate (DOP) by placing a small drop of neat DOP on the web and measuring the time for the drop to spread or wet the web (considered the time of failure). Webs which were not wet after two days were considered to be resistant indefinitely to DOP.

EXAMPLES 1–4

Comparative Examples C1–C5

In Examples 1–4, fluorinated compounds having several variations in fluorinated and fluorine-free monomer in their fluorochemical oligomeric portions were made and evaluated as polymer melt additives. In all cases, the molar monomer ratio of fluorinated monomer to fluorine-free monomer was kept constant at 4:1 (i.e., to give an $R_f/R_h$ ratio of 4:1 for each fluorinated compound) and the chain-transfer agent used was $HSCH_2CH_2COOCH_3$ ($R=C_1$) at a constant amount. Each fluorinated compound was melt-blended at 1% concentration with ESCORENE™ PP3505 polypropylene. Melt-blown nonwoven webs were made according to the Melt-Blown Extrusion Procedure, and each of the resulting webs was evaluated for repellency using the Water Repellency Test and the Oil Repellency Test, both initially and after annealing the webs for 10 minutes at 120° C. Also, the resistance time of the annealed nonwoven webs to dioctyl phthalate was measured using the DOP Wetting Time Test.

In Examples 3 and 4, the fluorinated compounds were copolymers of UNILIN™ 700A and MeFBSEA and MeFBSEMA, respectively (each having an $R_f$ chain length of $C_4$). In this case, each fluorinated compound was melt-blended at 2% concentration with PP3505 polypropylene.

In Comparative Examples C1 and C2, non-oligomeric fluorinated compounds having a high carbon number aliphatic moiety, an ester moiety-containing linking group but non-oligomeric (i.e., single chain) fluorochemical portion(s) were melt-blended at 1% concentration with PP3505. Melt-blown nonwoven webs were made according to the Melt-Blown Extrusion Procedure, and each web was evaluated as described in Examples 1–4. These non-oligomeric fluorinated compounds are repellent ester-containing polymer melt additives described in World Published Patent Applications WO 97/22659 and WO 99/05345, respectively.

In Comparative Examples C3 and C4, two fluorochemical oxazolidinones of the type described in U.S. Pat. No. 5,025,052, having non-oligomeric portions but known to be effective polymer melt additives, were melt-blended at 1% concentration with PP3505. Melt-blown nonwoven webs were made according to the Melt-Blown Extrusion Procedure, and testing of the modified PP3505 was conducted as described in Examples 1–4.

In Comparative Example C5, no polymer melt additive was incorporated into PP3505 prior to extruding the nonwoven web.

Results are presented in TABLE 1

TABLE 1

| Ex. | Fluorochemical Additive: Name | % | Initial: WR | Initial: OR | Annealed: WR | Annealed: OR | DOP Wet. Time |
|---|---|---|---|---|---|---|---|
| 1 | (MeFOSEA)$_4$(UNILIN™ 700A)$_1$-SCH$_2$CH$_2$COOCH$_3$ | 1 | 3 | 0.5 | 10 | 8 | >1 day |
| 2 | (MeFOSEA)$_4$(UNILIN™ 425A)$_1$-SCH$_2$CH$_2$COOCH$_3$ | 1 | 3 | 0 | 10 | 6 | >1 day |
| 3 | (MeFBSEA)$_4$(UNILIN™ 700A)$_1$-SCH$_2$CH$_2$COOCH$_3$ | 2 | 4 | 3 | 6.5 | 5.5 | 1 day |
| 4 | (MeFBSEMA)$_4$(UNILIN™ 700A)$_1$-SCH$_2$CH$_2$COOCH$_3$ | 2 | 4.5 | 1 | 7.5 | 5 | 1 day |
| C1 | MeFOSE-UNICID™ 700 | 1 | 4.5 | 0 | 5 | 0 | 10 sec. |
| C2 | (MeFOSE)$_2$-EMPOL™ 1008 | 1 | 7 | 1 | 9 | 2 | Immed. |
| C3 | FC Oxazolidinone A | 1 | 9 | 2 | 9 | 2 | >1 day |
| C4 | FC Oxazolidinone B | 1 | 3 | 0 | 7 | 0 | >1 day |
| C5 | No Additive | — | 2 | 0 | 2 | 0 | Immed. |

The data in TABLE 1 show that, in general for the annealed webs, the compounds of this invention imparted good to excellent water, oil and DOP resistance to polypropylene. The oil resistance after annealing was superior to that imparted by any of the comparative polymer melt additives.

EXAMPLES 5–8

In Examples 5–7 and Comparative Examples C6–C8, fluorochemical oligomeric compounds were made by copolymerizing MeFOSEA with ODA using hydrocarbon chain transfer agents having alkyl chain lengths varying in size from $C_1$ to $C_{50}$. For this study, the molar monomer ratio of MeFOSEA to ODA was kept constant at 4:1 (i.e., to give an $R_f/R_h$ ratio of 4:1 for each fluorinated compound). Each fluorinated compound was melt-blended at 1% concentration in ESCORENE™ PP3505 polypropylene. Melt-blown nonwoven webs were made according to the Melt-Blown Extrusion Procedure, and the resulting webs were evaluated for repellency using the Water Repellency Test and the Oil Repellency Test, both initially and after annealing the webs for 10 minutes at 120° C. Also, the resistance time of the annealed nonwoven webs to dioctyl phthalate was measured using the DOP Wetting Time Test.

In Example 8, the chain lengths of the hydrocarbon group and the aliphatic moiety were reversed from those in Example 7 (i.e., from $R_h=C_{18}$ and $R=C_{50}$ to $R_h=C_{50}$ and $R=C_{18}$). The resulting fluorinated compound was evaluated as described in Examples 5–7.

In Example C9, a fluorinated compound was made by copolymerizing MeFOSEA with ODA using a fluorochemical chain transfer agent. The resulting fluorinated compound was evaluated as described in Examples 5–7. Results are presented in TABLE 2.

TABLE 2

| Ex. | Fluorochemical Additive: Name | % | Initial: WR | OR | Annealed: WR | OR | DOP Wet. Time |
|---|---|---|---|---|---|---|---|
| C6 | (MeFOSEA)$_4$(ODA)$_1$-SCH$_2$CH$_2$COOCH$_3$ | 1 | 4 | 0 | 8.5 | 8 | >1 day |
| C7 | (MeFOSEA)$_4$(ODA)$_1$-SC$_{12}$H$_{25}$ | 1 | 5 | 0 | 8 | 3 | 5.5 hours |
| C8 | (MeFOSEA)$_4$(ODA)$_1$-SC$_{18}$H$_{37}$ | 1 | 4.5 | 0 | 8 | 1 | 5.5 hours |
| 5 | (MeFOSEA)$_4$(ODA)$_1$-SCH$_2$CH$_2$COO—C$_{22}$H$_{45}$ | 1 | 3.5 | 0 | 8.5 | 8 | >1 day |
| 6 | (MeFOSEA)$_4$(ODA)$_1$-SCH$_2$CH$_2$COO-UNILIN™ 425 | 1 | 3.5 | 0 | 10 | 7 | >1 day |
| 7 | (MeFOSEA)$_4$(ODA)$_1$-SCH$_2$CH$_2$COO-UNILIN™ 700 | 1 | 3.5 | 0 | 10 | 7 | >1 day |
| 8 | (MeFOSEA)$_4$(UNILIN™ 700A)$_1$-SC$_{18}$H$_{37}$ | 1 | 3 | 0.5 | 10 | 8 | >1 day |
| C9 | (MeFOSEA)$_4$(ODA)$_1$-SCH$_2$CH$_2$COO—MeFOSE | 1 | 3 | 0 | 9 | 2.5 | 2 min. |

The data from Examples 5–7 and Comparative Examples C6–C8 show that, for annealed webs, water repellency and resistance to wetting by DOP generally increased with increasing chain length of the alkyl group in the aliphatic moiety (R). The oil repellency and DOP resistance after annealing was greatest at the longest aliphatic moiety chain lengths ($C_{50}$, $C_{32}$ and $C_{22}$), dropping at intermediate chain lengths ($C_{18}$ and $C_{12}$), and increasing again at the shortest chain length ($C_1$).

The overall repellent performance imparted by the fluorochemical oligomeric compounds in Example 5–7, where R varied from a $C_{22}$ to a $C_{50}$ alkyl group, was surprising, exceeding the performance when R was a fluoroallyl group (Example C9). The same excellent performance was also noted when $R_h$ was the $C_{50}$ alkyl group (Example 8). Such oil repellency performance is unexpected from compounds containing such large oleophilic groups.

Comparative Example C10

EXAMPLE 9

In Comparative Example C10, a fluorochemical polymeric compound of high molecular weight was made by copolymerizing MeFBSEMA and UNILIN™ 700A at an $R_f/R_h$ molar ratio of 4/1 in MIBK as a solvent. The resulting fluorinated compound was melt-blended at 2% concentration in ESCORENE™ PP3505 polypropylene. A melt-blown nonwoven web was made according to the Melt-Blown Extrusion Procedure, and the resulting web was evaluated for repellency using the Water Repellency Test and the Oil Repellency Test, both initially and after annealing the web for 10 minutes at 120° C.

Results, presented in TABLE 3, show performance as a function of the molecular weight of the fluorinated compound. For comparison, Example 9 from TABLE 1, a fluorinated compound made by copolymerizing the monomers at the same 4/1 molar ratio but incorporating HSCH$_2$CH$_2$COOCH$_3$ as a chain transfer agent, was also included. This lower molecular weight fluorinated compound was also melt-blended at 2% concentration and evaluated using the same test procedures.

TABLE 3

| Ex. | Chain Transfer Agent | Initial: WR | OR | Annealed: WR | OR | DOP Wet. Time |
|---|---|---|---|---|---|---|
| C10 | MIBK | 2.5 | 0 | 3 | 0.5 | Immed. |
| 9 | HSCH$_2$CH$_2$COOCH$_3$ | 4.5 | 1 | 7.5 | 5 | 1 day |

The data in TABLE 3 show that overall performance is superior employing the lower molecular weight fluorochemical oligomeric compound.

We claim:

1. A fluorochemical oligomer having the structure:

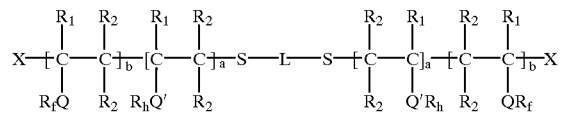

wherein the sum of a+b is an number such that the compound is oligomeric;

$R_1$ is hydrogen, halogen, or straight chain or branched chain alkyl containing 1 to about 4 carbon atoms;

each $R_2$ is independently hydrogen or straight chain or branched chain alkyl containing 1 to about 4 carbon atoms;

Q and Q' are each independently a covalent bond or an organic linking group, $R_f$ is a fluoroaliphatic group that comprises a fully fluorinated terminal group;

$R_h$ is a fluorine-free aliphatic group; and

X is a hydrogen atom or a group derived from a free radical initiator; and

L is a non-polymeric linking group.

2. The fluorochemical oligomer of claim 1 wherein at least one of said $R_h$ groups has 22 or more carbon atoms.

3. The fluorochemical oligomer of claim 1 wherein the ratio of $R_f$ groups to $R_h$ groups is at least 4:1.

4. The fluorochemical oligomer of claim 1 wherein $R_f$ has the structure $C_oF_{2o+1}$, where o is 4 to 14.

5. The fluorochemical oligomer of claim 1 wherein L is selected from the group of a covalent bond, straight chain, branched chain, or cyclic alkylene, arylene, aralkylene, oxy, oxo, thio, sulfonyl, sulfoxy, amino, imino, sulfonamido, carboxamido, carbonyloxy, urethanylene, ureylene, and combinations thereof.

6. The fluorochemical oligomer of claim 1 wherein L is chosen from the group consisting of a covalent bond,

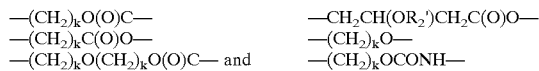

| —$(CH_2)_kO(O)C$— | —$CH_2CH(OR_2')CH_2C(O)O$— |
|---|---|
| —$(CH_2)_kC(O)O$— | —$(CH_2)_kO$— |
| —$(CH_2)_kO(CH_2)_kO(O)C$— and | —$(CH_2)_kOCONH$— | wherein each k is independently an integer from 0 to about 20, and $R_2'$ is alkyl of 1 to about 20 carbon atoms.

7. The fluorochemical oligomer of claim 1 comprising oligomerized units of compounds of the formula

8. A polymer composition comprising the fluorochemical oligomer of claim 1 and a thermoplastic or thermoset polymer.

9. The polymer composition of claim 8 wherein said thermoplastic polymer is selected from the group consisting of polyamides, acrylates, polyesters, polyurethanes, and polyolefins.

10. The composition of claim 8 wherein said fluorochemical oligomer comprises from 0.5 to 5 weight percent of said polymer composition.

11. A shaped article comprising the polymer composition of claim 8.

12. The shaped article of claim 11 wherein said fluorochemical oligomer comprises from 10 to 10,000 ppm fluorine.

13. The shaped article of claim 11 selected from the group of films, sheets and fibers.

14. An oily mist resistant electret filter medium comprising polypropylene electret fibers comprising the polymer composition of claim 9.

15. The filter medium of claim 14 wherein said fibers have an effective fiber diameter of 2 to 30 micrometers.

16. The filter medium of claim 14 wherein said fibers have been annealed.

17. The filter medium of claim 14 wherein said filter media has a basis weight of 10 to 100 g/m².

18. A fabric comprising the fibers of claim 13.

19. A medical gown comprising the fabric of claim 18.

20. The composition of claim 8 wherein said thermoset polymer is selected from the group consisting of polyurethanes, epoxy resins, epoxides and acrylates.

\* \* \* \* \*